(12) United States Patent
Durant et al.

(10) Patent No.: US 6,774,263 B1
(45) Date of Patent: Aug. 10, 2004

(54) PHARMACEUTICALLY ACTIVE COMPOUND AND METHODS OF USE

(75) Inventors: Graham J. Durant, Plymouth (GB); Michael Perlman, Brookline, MA (US); James B. Fischer, Cambridge, MA (US); Seetharamaiyer Padmanabhan, Lexington, MA (US)

(73) Assignee: Cambridge Neuroscience, Inc., Cambridge, MA (US)

( * ) Notice: Subject to any disclaimer, the term of this patent is extended or adjusted under 35 U.S.C. 154(b) by 0 days.

(21) Appl. No.: 09/169,028

(22) Filed: Oct. 9, 1998

Related U.S. Application Data (60) Provisional application No. 60/063,469, filed on Oct. 10, 1997.

(51) Int. Cl.[7] .................. C07C 279/18; A61K 31/155
(52) U.S. Cl. .................. 564/238; 564/230; 564/237; 514/634
(58) Field of Search .................. 564/230, 237, 564/238, 229, 239; 514/634, 633, 524, 311; 546/152

(56) References Cited

U.S. PATENT DOCUMENTS

| | | | |
|---|---|---|---|
| 5,336,689 A | 8/1994 | Weber et al. | 514/634 |
| 5,574,070 A | 11/1996 | Keana et al. | 514/634 |
| 5,622,968 A | 4/1997 | Goldin et al. | 514/313 |
| 5,637,622 A | 6/1997 | Weber et al. | 514/634 |
| 5,637,623 A | 6/1997 | Goldin et al. | 514/634 |
| 5,652,269 A | 7/1997 | Goldin et al. | 514/632 |
| 5,670,519 A | 9/1997 | Goldin et al. | 514/313 |
| 5,672,608 A | 9/1997 | Goldin et al. | 514/313 |
| 5,686,495 A | 11/1997 | Goldin et al. | 514/632 |
| 5,922,772 A | 7/1999 | Durant et al. | 514/634 |
| 6,156,741 A | * 12/2000 | Durant et al. | 514/150 |

FOREIGN PATENT DOCUMENTS

| | | |
|---|---|---|
| WO | WO 94/27591 | 12/1994 |
| WO | WO 97/30054 | 8/1997 |

OTHER PUBLICATIONS

Int'l Search Report dated Feb. 22, 1999 re Int'l Appln. No. PCT/US98/21395.

* cited by examiner

*Primary Examiner*—Shailendra Kumar
(74) *Attorney, Agent, or Firm*—Edwards & Angell, LLP; Jeffrey D. Hsi (57) ABSTRACT

This invention relates to racemic and optically active N-(2-chloro-5-methylthiophenyl)-N'-(3-methylsulfinylphenyl)-N'-methylguanidine, N-(2-chloro-5-methylsulfinylphenyl)-1-(7-trifluoromethyl-1,2,3,4-tetrahydroquinolinyl) carboximidamide, and N-(3-methylsulfinylphenyl)-N-methyl-N'-(2-chloro-5-methoxyphenyl)guanidine and pharmaceutically acceptable salts thereof, and pharmaceutical compositions and therapeutic methods of treatment that comprise such compounds. Compounds of the invention are particularly useful for the treatment or prophylaxis of neurological injury and neurodegenerative disorders.

8 Claims, 3 Drawing Sheets

PHARMACEUTICALLY ACTIVE COMPOUND AND METHODS OF USE

CROSS REFERENCE TO RELATED APPLICATION

The present application is a continuation-in-part of U.S. provisional application Ser. No. 60/063,469, filed Oct. 10, 1997, which is incorporated herein by reference in its entirety.

BACKGROUND OF THE INVENTION

1. Field of the Invention

The present invention is directed to N-(2-chloro-5-methylthiophenyl)-N'-(3-methylsulfinylphenyl)-N'-methylguanidine, N-(2-chloro-5-methylsulfinylphenyl)-1-(7-trifluoromethyl-1,2,3,4-tetrahydroquinolinyl)carboximidamide, and N-(3-methylsulfinylphenyl)-N-methyl-N'-(2-chloro-5-methoxyphenyl)guanidine and pharmaceutically acceptable salts thereof, and pharmaceutical compositions and therapeutic methods of treatment that comprise such compounds ("compounds of the invention"). The compounds of the invention are particularly useful for the treatment or prophylaxis of neurological injury and neurodegenerative disorders.

2. Background

A number of substituted guanidines have been reported. See, e.g., U.S. Pat. Nos. 1,411,731, 1,422,506, 1,597,233, 1,642,180, 1,672,431, 1,730,388, 1,756,315, 1,795,739, 1,850,682, 2,145,214, 2,254,009, 2,633,474, 3,117,994, 3,140,231, 3,159,676, 3,228,975, 3,248,426, 3,252,816, 3,283,003, 3,270,054, 3,301,755, 3,320,229, 3,301,775, 3,409,669, 3,479,437, 3,547951, 3,639,477, 3,681,457, 3,769,427, 3,784,643, 3,803,324, 3,908,013, 3,949,089, 3,975,533, 3,976,787, 4,060,640, 4,014,934, 4,161,541, 4,709,094, 4,906,779, 5,093,525, and 5,190,976; PCT applications WO 90/12575, WO 91/12797, WO 91/18868, WO 92/14697, WO 94/14461, WO 94/27591, WO 95/14467, WO 95/20950, H. W. Geluk, et al., *J. Med. Chem.*, 12:712 (1969), and N. L. Reddy et al., *J. Med. Chem.*, 37:260–267 (1994). WO 94/27591 discloses inter alia N-(2-chloro-5-methylthiophenyl)-N'-(3-methylthiophenyl)-N'-methylguanidine.

Nerve cell death (degeneration) can cause potentially devastating and irreversible effects for an individual and may occur e.g. as a result of stroke, heart attack or other brain or spinal chord ischemia or trauma. Additionally, nerve cell death (degeneration) occurs with neurodegenerative disorders such as Alzheimer's disease, Parkinson's disease, Huntington's disease, Amyotrophic Lateral Sclerosis, Down's Syndrome and Korsakoff's disease.

Therapies have been investigated to treat nerve cell degeneration and related disorders, e.g., by limiting the extent of nerve cell death that may otherwise occur to an individual.

The compound MK-801 has exhibited good results in a variety of in vivo models of stroke. See B. Meldrum, *Cerbrovascular Brain Metab. Rev.*, 2:27–57 (1990); D. Choi, *Cerbrovascular Brain Metab. Rev.*, 2:105–147 (1990). See also Merck Index, monograph 3392, 11th ed., 1989. For example, MK-801 exhibits good activity in mouse audiogenic tests, a recognized model for evaluation of neuroprotective drugs. See, e.g., M. Tricklebank et al., *European Journal of Pharmacology*, 167:127–135 (1989); T. Seyfried, *Federation Proceedings*, 38(10):2399–2404 (1979).

However, MK-801 also has shown toxicity and further clinical development of the compound is currently uncertain. See J. W. Olney et al., *Science*, 244:1360–1362 (1989); W. Koek et al., *J. Phamacol. Exp. Ther.*, 252:349–357 (1990); F. R. Sharp et al., *Society for Neuroscience Abstr.*, abstr. no. 482.3 (1992).

It thus would be highly desirable to have new neuroprotection therapies.

SUMMARY OF THE INVENTION

In a first preferred aspect, the present invention provides N-(2-chloro-5-methylthiophenyl)-N'-(3-methylsulfinylphenyl)-N'-methylguanidine, and pharmaceutically acceptable salts thereof, i.e. the compound of the following structure (I):

and pharmaceutically acceptable salts thereof. References herein to "compound (I)" refer to the compound of the above structure as well as pharmaceutically acceptable salts of N-(2-chloro-5-methylthiophenyl)-N'-(3-methylsulfinylphenyl)-N'-methylguanidine.

The invention also includes optically enriched mixtures of compound (I). As can be seen from the above structure, the sulfur of the 3-methylsulfinyl group is chiral. An optically enriched mixture of compound (I) contains substantially more (e.g. about 60 mole %, 70 mole %, 80 mole % or 90 mole % or more) of one enantiomer than the other enantiomer. For use in the therapeutic methods of the invention, preferably a substantially pure optically active mixture is employed, e.g. a mixture containing at least about 92 mole %, or 95 mole % or even 97 mole %, 98 mole % or 99 mole % or more of one enantiomer of compound (I).

More specifically, the invention includes following optically active (−)-N-(2-chloro-5-methylthiophenyl)-N'-(3-methylsulfinylphenyl)-N'-methylguanidine (referred to herein, and shown below as compound (IA)) and (+)-N-(2-chloro-5-methylthiophenyl)-N'-(3-methylsulfinylphenyl)-N'-methylguanidine (referred to herein, and shown below as compound (IB)).

Compound (I) (which includes compounds I(A) and/or compound I(B)) has been found to exhibit potent neuroprotective activity. References herein to "compound (I)" are intended to also refer to compound I(A) and/or compound I(B) unless otherwise specified. Those optically active compounds also can be identified as (R)-N-(2-chloro-5-methylthiophenyl)-N'-(3-methylsulfinylphenyl)-N'-methylguanidine (referred to herein, and shown below as compound (IA)) and (S)-N-(2-chloro-5-methylthiophenyl)-N'-(3-methylsulfinylphenyl)-N'-methylguanidine, pursuant to the Cahn-Ingold-Prelog convention.

Compound (I) also has been surprisingly found to exhibit significantly decreased untoward behavioral effects in a number of in vivo assays, including Irwin tests and rat rotarod motor coordination tests. See the results of Examples 8 and 9 which follow.

In a further aspect, the invention provides the compound N-(2-chloro-5-methylsulfinylphenyl)-1-(7-trifluoromethyl-1,2,3,4-tetrahydroquinolinyl) carboximidamide, and pharmaceutically acceptable salts thereof, i.e. the compound of the following structure (II):

(II)

and pharmaceutically acceptable salts thereof References herein to "compound (II)" refer to the compound of the above structure as well as pharmaceutically acceptable salts of N-(2-chloro-5-methylsulfinylphenyl)-1-(7-trifluoromethyl-1,2,3,4-tetrahydroquinolinyl) carboximidamide.

The invention includes both racemic mixtures and optically enriched mixtures of compound (II). An optically enriched mixture contains substantially more (e.g., about 60 mole %, 70 mole %, 80 mole %, 90 mole % or 95 mole % or 98 mole % or more) of one enantiomer of compound (II) than the other stereoisomer. For use in the therapeutic methods of the invention, preferably a substantially pure optically active mixture is employed, e.g. a mixture containing at least about 92 mole %, or 95 mole % or even 97 mole %, 98 mole % or 99 mole % or more of one enantiomer of compound (II).

In a yet further aspect, the invention provides the compound N-(3-methylsulfinylphenyl)-N-methyl-N'-(2-chloro-5-methoxyphenyl)guanidine, and pharmaceutically acceptable salts thereof, i.e. the compound of the following structure (III):

(III)

and pharmaceutically acceptable salts thereof. References herein to "compound (III)" refer to the compound of the above structure as well as pharmaceutically acceptable salts of N-(3-methylsulfinylphenyl)-N-methyl-N'-(2-chloro-5-methoxyphenyl)guanidine.

The invention includes both racemic mixtures and optically enriched mixtures of compound (III). An optically enriched mixture contains substantially more (e.g., about 60 mole %, 70 mole %, 80 mole %, 90 mole % or 95 mole % or 98 mole % or more) of one enantiomer of compound (III) than the other stereoisomer. For use in the therapeutic methods of the invention, preferably a substantially pure optically active mixture is employed, e.g. a mixture containing at least about 92 mole %, or 95 mole % or even 97 mole %, 98 mole % or 99 mole % or more of one enantiomer of compound (III).

It has been found that compounds (I), (II) and (III) are each useful for a number of therapeutic applications. In particular, the invention includes methods for treatment and/or prophylaxis of neurological conditions/injuries such as epilepsy, neurodegenerative conditions and/or nerve cell death (degeneration) resulting from e.g. hypoxia, hypoglycemia, brain or spinal chord ischemia, retinal ischemia, brain or spinal chord trauma or post-surgical neurological deficits and the like as well as neuropathic pain. The compounds of the invention are especially useful for treatment of a person susceptible or suffering from stroke or heart attack or neurological deficits relating to cardiac arrest, a person suffering or susceptible to brain or spinal cord injury, or a person suffering from the effects of retinal ischemia or degeneration. Compounds (I), (II) and (III) also are each useful to treat and/or prevent various neurodegenerative diseases such as Parkinson's disease, Huntington's disease, Amyotrophic Lateral Sclerosis, Alzheimer's disease, Down's Syndrome, Korsakoff's disease, cerebral palsy and/or age-dependent dementia. Compounds (I), (II) and (III) will be further useful to treat and/or prevent migraines, shingles (herpes zoster), epilepsy, emesis and/or narcotic withdrawal symptoms. Also, in addition to treatment of retinal ischemia and related disorders, the invention provides methods for treatment of optic nerve injury/damage. The treatment methods of the invention in general comprise administration of a therapeutically effective amount of compound (I), (II) and/or (III) to an animal, including a mammal, particularly a human in need of treatment.

The invention also provides pharmaceutical compositions comprising a therapeutically effective amount of compound (I), (II) and/or (III) and a pharmaceutically acceptable carrier.

Other aspects of the invention are disclosed infra.

DETAILED DESCRIPTION OF THE INVENTION

Compound (I) may be suitably prepared as described in Example 1 which follows and which includes preparation of 3-methylsulfinyl-N-methylaniline by oxidation of N-methyl-3-methylthioaniline. A variety of oxidants may be employed, e.g. $H_2O_2$, sodium periodate and the like. Hydrogen peroxide may be preferred because it can provide a final product (compound (I)) that exhibits enhanced aqueous solution solubility relative to the product of a periodate oxidation. An asymmetric oxidation also may be conducted to provide the optically active sulfinyl (SO) moiety. See, for example, the procedure disclosed in F. A. Davis et al., *J. Org. Chem.*, 57:7274–7285 (1992). See also the procedures set forth in Example 5 which follows. Also, optically active compound (IA) or (IB), or an optically precursor compound such as 3-methylsulfinyl-N-methylaniline, where the sulfinyl group is selectively either of the (R) or (S) configuration can be obtained by column chromatography using an optically active binding material, or the racemic compound (I) can be separated into optically active (+) and (−) enantiomers by such column chromatography and optically active binding material. See, for instance, the procedure disclosed in Example 2 which follows.

After the oxidation step, the aniline salt then is suitably formed and that salt reacted with 2-chloro-5-methylthiophenylcyanamide. The crude compound (I) can be purified as desired, e.g. by column chromatography.

Compound (II) can be suitably prepared as generally described in published PCT Application WO 97/30054 (PCT/US97/02678). In particular, 2-chloro-5-methylsulfinylphenylcyanamide can be reacted with 7-trifluoromethyl-1,2,3,4-tetrahydroquinoline (the tetrahydroquinoline typically in salt form such as a hydrochloride or mesylate salt) in a suitable solvent such as chlorobenzene or toluene under an inert atmosphere (e.g. argon or nitrogen) with heating (e.g. reflux temperature) until reaction completion, e.g. 2 or more hours. Additionally, 2-chloro-5-methylthiophenylcyanamide can be reacted under similar conditions with 7-trifluoromethyl-1,2,3,4-tetrahydroquinoline to form N-(2-chloro-5-methylthiophenyl)-1-(7-trifluoromethyl-1,2,3,4-tetrahydroquinolinyl) carboximidamide, which can be then oxidized to form the desired compound (II). Suitable oxidants include e.g. $H_2O_2$ and sodium periodate. See Example 3 which follows for exemplary conditions. Optically active stereoisomers of compound (II) can be produced as described above for compound (I), i.e. an asymmetric oxidation may be conducted to provide the optically active sulfinyl (SO) moiety (see F. A. Davis et al., supra), or an optically precursor compound such as 2-chloro-5-methylsulfinylanidine, where the sulfinyl group is selectively either of the (R) or (S) configuration can be obtained by column chromatography using an optically active binding material. Racemic compound (II) also can be separated into optically active (+) and (−) enantiomers by use of such column chromatography and optically active binding material.

Compound (III) can be suitably prepared as generally described in published PCT Application WO 94/27591 (PCT/US94/06008). In particular, N-methyl-3-methylsulfinylanidine can be reacted with 2-chloro-5-methoxyphenylcyanamide in a suitable solvent such as chlorobenzene or toluene under an inert atmosphere (e.g. argon or nitrogen) with heating (e.g. reflux temperature) until reaction completion, e.g. 2 or more hours. Additionally, N-methyl-3-methylthioaniline can be reacted under similar conditions with 2-chloro-5-methoxyphenylcyanamide to form N-(3-methylthiophenyl)-N-methyl-N'-(2-chloro-5-methoxyphenyl)guanidine, which can be then oxidized to form the desired compound (III). Suitable oxidants include e.g. $H_2O_2$ and sodium periodate. See Example 4 which follows for exemplary conditions. Optically active stereoisomers of compound (III) can be produced as described above for compound (I), i.e. an asymmetric oxidation may be conducted to provide the optically active sulfinyl (SO) moiety (see F. A. Davis et al., supra), or an optically precursor compound such as N-methyl-3-methylsulfinylaniline, where the sulfinyl group is selectively either of the (R) or (S) configuration can be obtained by column chromatography using an optically active binding material. Racemic compound (III) also can be separated into optically active (+) and (−) enantiomers by use of such column chromatography and optically active binding material.

As discussed above, the present invention includes methods for treatment and/or prophylaxis of certain neurological disorders, including the consequences of stroke, heart attack and traumatic head or brain injury, epilepsy or neurodegenerative diseases comprising the administration of an effective amount of compound (I), (II) and/or (III) of the invention to a subject including a mammal, particularly a human, in need of such treatment. In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include e.g. heart attack, stroke and/or persons suffering from cardiac arrest, neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure involving extra-corporal circulation such as e.g. a bypass procedure. Neurodegenerative diseases that may be treated by a compound of the invention include Parkinson's disease, Huntington's disease, Amyotrophic Lateral Sclerosis, Alzheimer's disease, Down's Syndrome and Korsakoff's disease.

The invention in particular provides therapeutic methods which comprise administration of compound (I), (II) and/or (III) of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurism or hemorrhage. Thus, an effective amount of compound (I), (II) and/or (III) of the invention could be administered pre-operatively or peri-operatively to reduce such risks associated with carotid endarterectomy, or other post-surgical neurological deficits.

The invention further includes methods for prophylaxis against neurological deficits resulting from e.g. coronary artery bypass graft surgery and aortic valve replacement surgery, or other procedure involving extra-corporal circulation. Those methods will comprise administering to a patient undergoing such surgical procedures an effective amount of compound (I), (II) and/or (III) of the invention, typically either pre-operatively or peri-operatively.

The invention also provides methods for prophylaxis and treatment against neurological injury for patients undergoing myocardial infarction, a procedure that can result in ischemic insult to the patient. Such methods will comprise administering to a patient undergoing such surgical procedure an effective amount of compound (I), (II) and/or (III) of the invention, typically either pre-operatively or peri-operatively.

Also provided are methods for treating or preventing neuropathic pain such as may experienced by cancer patients, persons having diabetes, amputees and other persons who may experience neuropathic pain. These methods for treatment comprise administration of an effective amount of compound (I), (II) and/or (III) of the invention to a patient in need of such treatment.

The invention also provides methods for treatment and prophylaxis against eye disorders and injury, including methods for treatment of reduced flow of blood or other nutrients to retinal tissue or optic nerve, methods for treatment of retinal ischemia and trauma and associated disorders, and methods for treatment of optic nerve damage/injury. Disorders associated with retinal or optic nerve injury or ischemia that may be treated in accordance with the invention include e.g. diabetes, significantly elevated intraocular pressures and glaucoma, diseases such as to retinal artery or vein occlusion, atherosclerosis, venous capillary insufficiency, senile macular degeneration and cystoid macular edema. In such methods, a compound of the invention can be administered parenterally or by other procedure as described herein to a subject suffering from or susceptible to ischemic insult or other injury or disorder that may adversely affect visual function. Post-ischemic or post-injury administration also may limit retinal damage. Intravitreal injection of a compound of the invention also may be a preferred administration route to provide more direct treatment to the injured retina or optic nerve.

The invention also provides methods for treatment of a subject suffering from shingles as well as treatment of a person suffering from or susceptible to migraines, particularly to alleviate the pain and discomfort associated with those disorders. These methods comprise administration of an effective amount of compound (I), (II) and/or (III) of the invention to a patient in need of treatment.

The invention further provides a method of treating Korsakoff's disease, a chronic alcoholism-induced condition, comprising administering to a subject including a mammal, particularly a human, compound (I), (II) and/or (III) in an amount effective to treat the disease. Compounds of the invention are each anticipated to have utility for the attenuation of cell loss, hemorrhages and/or amino acid changes associated with Korsakoff s disease.

As discussed above, the invention also includes methods for treating a person suffering from or susceptible to cerebral palsy, emesis, narcotic withdrawal symptoms and age-dependent dementia, comprising administering to a subject including a mammal, particularly a human, compound (I), (II) and/or (III) in an amount effective to treat the condition.

For at least some therapeutic methods of the invention, it may be preferred to use an optically enriched mixture of compound (I), (II) (III). In particular, it may be preferred to use compound (IB), which appears to exhibit enhanced therapeutic activity relative to the (−) enantiomer. See, for instance, the results set forth in the examples which follow.

Compound (I), (II) or (III) of the invention may be used in therapy in conjunction with other medicaments. For example, for treatment of a stroke victim or a person susceptible to stroke, compound (I), (II) or (III) may be suitably administered together with a pharmaceutical targeted for interaction in the blood clotting mechanism such as streptokinase, tPA, urokinase and other agents that lyse clots. Also, compound (I), (II) or (III) may be administered together with agents such as heparin and related heparin-based compounds, acenocoumarol or other known anticoagulants. Compounds (I), (II) and (III) may be used singularly in a pharmaceutical formulation, or two or all three of compounds (I), (II) and (III) may be used in combination, e.g. in the same or different pharmaceutical formulations, or sequentially. However, preferably such a combination therapy will entail substantially simultaneous administration of two or all three of compounds (I), (II) and (III) to a patient, e.g. in a unitary pharmaceutical composition containing the compounds.

The invention also includes methods for treatment of various pain, e.g. migraines, chronic pain, and the like, comprising administering to a subject, particularly a mammal such as a human, in need of such treatment, e.g. a subject that is suffering from migraines, chronic pain, or other pain, an effective amount of a compound of the invention.

The invention also includes methods for treatment of infections, including Gram-negative and Gram-positive bacterial infections, comprising administering a combination of 1) an aminoglycoside antibiotic, and 2) a compound (I), (II) and/or (IV) as defined herein. A wide variety of aminoglycoside antibiotics are suitable for use in the formulations of the invention. Typically, suitable aminoglycoside antibiotics contain two or more amino sugars (aminoglycosides) connected to an amino-cyclitol nucleus. Exemplary aminoglycoside antibiotics preferred for use in formulations of the present invention include clinical agents such as gentamycin, amikacin, kanamycin, streptomycin, paromoycin, neomycin, netilmicin and tobramycin. Other suitable aminoglycosides include seldomycins, sisomycins, aurimycin, lividomycins, streptothricins, hybrimycins, coralinomycin, butirosin, strepomutins, nebramycins, tenebrimycins, ribostamycins, destomycins, trehalosamines, myomycins, fortimicins, mutamicins and kasugamycin. Suitable aminoglycoside antibiotics are also disclosed in U.S. Pat. Nos. 5,508,269; 4,645,760; and 4,380,625. It should be appreciated however that the present invention is not limited by any particular aminoglycoside antibiotic, and the invention is applicable to any aminoglycoside antibiotic now known or subsequently discovered or developed. The aminoglycoside and compound (I), (II) and/or (III) may be administered simultaneously, in the same or different pharmaceutical formulations, or sequentially. Preferably, the components of the combination are administered substantially simultaneously, e.g. in a unitary pharmaceutical composition containing the two components. Preferred methods and compositions that comprise an aminoglycoside in combination with compound (I), (II) and/or (III) will be effective against infections previously treated with aminoglycoside antibiotics, but with the significant advantage of decreased occurrence of ototoxicity relative to use of an aminoglycoside antibiotic alone.

The invention also provides methods in vitro and in vivo binding activity diagnostic methods using a radiolabelled form of compound (I), (II) or (II) , e.g., compound (I), (II) or (III) that is labeled with tritium, $^{125}I$ or the like. Such a labeled compound (I), (II) or (III) can be administered to a mammal and the subject then scanned for binding of the compound. Specifically, single photon emission computed tomography ("SPECT") can be employed to detect such binding. Such an analysis of the mammal could e.g. aid in the diagnosis and treatment of acute cerebral ischemia. That is, labeled compound (I) will selectively bind to ischemic tissue of e.g. a subject's brain to differentiate between ischemic and non-ischemic tissue and thereby assess trauma or other injury to the brain. Accordingly, the invention also includes compound (I), (II) or (III) that is in a radiolabelled form such as tritium or $^{125}I$.

Compounds of the invention can be administered intranasally, orally or by injection, e.g., intramuscular, intraperitoneal, subcutaneous or p(t intravenous injection, or by transdermal, intraocular or enteral means. The optimal dose can be determined by conventional means. A compound of the invention is suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

A compound of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are generally preferred.

It will be appreciated that the actual preferred amounts of a compound of the invention used in a given therapy will vary according to the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of compound (I), (II) or (III) will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage, preferably from 0.2 to 2 milligrams per unit dosage.

As with prior guanidines such as those reported in U.S. Pat. No. 1,411,713, compounds of the invention should have utility as rubber accelerators.

The entire text of all documents cited herein are incorporated herein by reference. The invention is further illustrated by the following non-limiting examples.

EXAMPLE 1

Preparation of (±)-N-(2-chloro-5-methylthiophenyl)-N'-(3-methylsulfinylphenyl)-N'-methylguanidine hydrocloride Part 1. Preparation of 3-methylsulfinyl-N-methylaniline To a well cooled (ice bath) solution of N-methyl-3-methylthioaniline (30.4 g, 198.4 mmol) in acetone (250 ml) was added dropwise hydrogen peroxide (25%, 92 ml) over a period of 15 minutes. The reaction mixture was stirred for 2 hours and concentrated under reduced pressure to remove acetone. The reaction mixture was diluted with water (200 ml) and repeatedly extracted with ethyl acetate (3×100 ml). Combined organic extracts were washed with sodium thiosulfate solution (10%, 50 ml), dried and concentrated to afford the crude reaction mixture. The residue was chromatographed on silica gel using gradually mixtures of hexanes:ethyl acetate initially 4:1, and later 3:2. These elutions removed most of the unreacted starting material and most of the sulfone formed. Finally elution with ethyl acetate and later ethyl acetate containing 5% methanol eluted the sulfoxide and the fractions were combined, concentrated under reduced pressure to yield the sulfoxide as an oil (19 g, 57%); TLC ($CHCl_3$:MeOH; 19:1); Rf=0.48; $^1$H-NMR ($CDCl_3$) δ 2.69 (s, 3H, S(O)Me), 2.86 (s, 3H, NMe), 6.67 (dd, 1H), 6.81 (dd, 1H), 6.92 (d, 1H), 7.27 (m, 1H) HPLC 98.6% @ 8.6 minutes.

Part 2. Preparation of 3-methylsulfinyl-N-methylaniline hydrocloride

The free amine, (11.66 g, 68.90 mmol), obtained in Part 1 above, was dissolved in dichloromethane (100 ml; cooled in ice cold water (5–10° C.)) and to that solution anhydrous hydrogen chloride in ether (1M, 80 ml) was added slowly with vigorous stirring to enable thorough mixing. After the addition was complete, the mixture was stirred for 30 minutes, and then concentrated under reduced pressure and dried under high vacuum to afford the hydrochloride salt as hygroscopic yellow fluffy solid in almost quantitative yield. $^1$H-NMR ($CD_3OD$) δ 2.87 (s, 3H, S(O)Me), 3.15 (s, 3H, NMe) 7.65 (m, 1H), 7.77 (m, 1H), 7.83 (m, 1H); HPLC 98.6% @ 8.63 minutes.

Part 3. Preparation of (±)-N-(2-chloro-5-methylthiophenyl)-N'-(3-methylsulfinylphenyl)-N'-methylguanidine hydrocloride

2-chloro-5-methylthiophenylcyanamide (9.28 g, 46.7 mmol) and toluene (50 ml) was added to a solution of 3-methylsulfinyl-N-methylaniline hydrochloride (7.17 g, 34.85 mmol) in dichloromethane (50 ml). This mixture was slowly heated in an oil bath to 135–140° C. and the dichloromethane distilled was collected. After the complete distillation of dichloromethane the reaction mixture was maintained at 135–140° C. for 1 hour, then cooled to room temperature and the solvent was removed under reduced pressure. The residue was purified by silica gel column chromatograph using initially chloroform and gradually to chloroform containing 5% methanol as eluents. The title compound was obtained as a light colored product upon concentration of fractions was dried under high vacuum (5.45 g, 39%); mp: 148–154° C.; HPLC 93.2 % @ 14.3 minutes; TLC (CHCl₃:MeOH; 4:1); Rf=0.33 ¹H-NMR (CD₃OD) δ 2.46 (s, 3H, SMe), 2.82 (s, 3H, S(O)Me), 3.53 (s, 3H, NMe), 7.19 (s, 1H), 7.21 (d, 1H), 7.40 (dd, 1H), 7.65 (m, 1H), 7.70 (m, 2H), 7.81 (d, 1H); Anal. Calcd. for $C_{16}H_{19}Cl_2N_3OS_2 \cdot 1.5\ H_2O$; C:44.55, H: 5.14, N:9.27, S:14:37; Found: C: 44.23, H:4.75, N:9.35, S:14.09. Example 2 Resolution of (±)-N-(2-chloro-5-methylthiophenyl)-N'-(3-methylsulfinylphenyl)-N'-methylguanidine (compound (I)) to provide(−)-N-(2-chloro-5-methylthiophenyl)-N'-(3-methylsulfinylphenyl)-N'-methylguanidine (compound (IA)) and (+)-N-(2-chloro-5-methylthiophenyl)-N'-(3-methylsulfimylphenyl)-N'-methylguanidine (compound (IB)). 2.25g of the free base of (±)-N-(2-chloro-5-methylthiophenyl)-N'-(3-methylsulfinylphenyl)-N'-methylguanidine was dissolved in ethanol and chromatographed on a Chiralpak AD column (2×25 cm, Diacel Chemical Ind.) at 40° C. using 100% ethanol as eluent, and UV detection at 300 nm. The (−) enantiomer of compound (I), i.e. compound (IA), eluted first followed by the (+) enantiomer of compound (a), i.e. compound (IB). The fractions corresponding to pure enantiomers were pooled and evaporated to provide 1.07 g of compound (IA) and 1.01 g of compound (IB) (yields of 95% and 90%, respectively) as resins (free base) that crystallized at 4° C. Analysis on a Chiralpak AD analytical column (4.6×250 mm; 100% ethanol mobile phase) showed that compound (IA) was obtained in 99.8% ee and compound (IB) was obtained at 98.6% ee (retention times of 8.5 minutes and 16 minutes, respectively). Purities were further evaluated by reversed phase HPLC (Ultrasphere ODS column), 5 micron, 4.6×25 cm; 220 nm; 30 minute linear gradient; 2 to 98% AcCN is water/0/1% TFA). Compound (IA) was found to be 99.0% pure, and compound (IB) was found to be 98.7% pure. Proton NMR showed trace of ethanol as only impurity.

EXAMPLE 3

Preparation of N-(2-chloro-5-methylsulfinylphenyl) 1-(1,2,3, 4-tetrahydroquinolinyl)carboxamidamide Part 1: Preparation of 7-trifluoromethyl-1,2,3,4-tetrahydroquinotine hydrocloride A solution of 4-chloro-7-trifluoromethylquinoline (15 g, 64.8 mmole) in methanol (75 ml) was added platinum (IV) oxide (1.5 g, 10% w/w) in a 250 ml Parr reaction vessel. The slurry was hydrogenated at 45–50 psi for 5–6 hours. The catalyst was filtered (Fire hazard!) and the clean filtrate was concentrated in vacuo to afford the product as the hydrochloride salt, a white solid, yield 15.3 g; mp: 164–168° C.; HPLC 99% @ 20.6 minutes; ¹H-NMR (CD₃OD) δ 5 2.27 (m, 2H, CH₂), 2.95 (t, 2H, CH₂), 3.58 (t, 2H, CH2), 7.37 (d, 2H, ArH), 7.57 (d, 1H, ArH), 7.91 (s, 1H, ArH).

Part 2: Preparation of N-(2-chloro-5-methylthiophenyl)-1-(7-trifluoromethyl-1,2,3,4-tetrahydroquinoline) carboxamidamide Condensation of 2-chloro-5-methylthiophenylcyanamide (2.4 g, 12 mmol) and 1,2,3,4-tetrahydroquinolinehydrochloride (2.0 g, 8.4 mmol) in dichloromethane (5 ml) and xylenes (5 ml) was carried out as described in Example 1, Part 3 above to provide N-(2-chloro-5-methylthiophenyl)-1-(7-trifluoromethyl-1,2,3,4-tetrahydroquinoline)carboxamidamide: Yield 54%; mp: 128–132° C.; HPLC 96% @ 21.1 minutes; TLC (CHCl₃:MeOH; 9:1); Rf=0.57; ¹H-NMR (CD₃OD) δ 2.07 (t, 2H, CH₂), 2.47 (s, 3H, SMe), 2.89 (t, 3H, CH₂), 3.83 (t, 2H, CH₂), 6.98 (m, 2H, ArH), 7.36 (m, 3H, ArH), 7.82 (s, 1H, ArH).

Part 3. Preparation of N-(2-chloro-5-methysulfinylphenyl)-1-(1,2,3,4-tetrahydroquinolinyl)carboxamidamide To a solution of N-(2-chloro-5-methylthiophenyl)-1-(7-trifluoromethyl-1,2,3,4-tetrahydroquinoline) carboxamidamide (1 g, 2.29 mmol) pepared in Part 2 above of this Example in 10 ml of methanol and water (5 ml) sodium periodate (1.3 g, 6.08 mmol) was added and the solution stirred overnight. Upon filitering the solid separated, the solid was washed with dichloromethane (10 ml) and the filtrate was concentrated to remove methanol and dichloromethane. The solution was made basic to pH -12 with sodium hydroxide (1N, 25 ml) and extracted repeatedly with chloroform (3×20 ml). Filtered to remove any solid separated, washed with organic layer with water (20 ml), dried and concentrated the organic layer to give the crude product. The free base (0.75 g), obtained was purified by column chromatography eluting initially with methanol and gradually to chloroform containing methanol (5%) to give the pure product. The pure product was dissolved in methanol (10 ml), cooled in ice-water bath and was added 12 ml of ethereal solution of hydrogen chloride (1M). After stirring for 30 minutes the reaction mixture was concentrated, coevaporated twice with 10 ml of dichloromethane to give the hydrochloride salt as a white solid and dried under high vacuum. Yield 0.78 g (73%) mp: 144–148° C.; HPLC 93% @ 16.7 minutes; TLC (CHCl₃:MeOH; 9:1); Rf=0.63; ¹H-NMR (CD₃OD) δ 2.18 (t, 2H, CH₂), 2.81 (s, 3H, SOMe), 2.89 (t, 3H, CH2), 3.96 (t, 2H, CH₂), 7.45 (s, 2H ArH), 7.75 (s, 4H, ArH).

EXAMPLE 4

Preparation of N-(2-chloro-5-methoxyphenyl)-N'-(3-methylsulfinylphenyl)-N'-methylguanidine hydrocloride Part 1: N-Methyl-N-cyano-3-methylthioaniline

A suspension of N-methyl-3-methylthioaniline (1.53 g, 10 mmol) in water (50 ml) containing sodium bicarbonate (0.9 g, 11 mmole) cyanogen bromide (1.1 g, 11 mmol) was stirred overnight. The reaction mixture was extracted repeatedly with ethyl acetate 13×15 ml) and the organic layer was washed with water (2×10 ml), dried over magnesium sulfate and concentrated to give the product, 1.5 g (84%); oil; TLC (Hexanes:EtOAc; 85:15); Rf=0.33; $^1$H-NMR (CDCl$_3$) δ 2.48 (s, 3H, SCH3), 3.32 (s, 3H, NMe), 6.83 (d, 1H, ArH), 6.93 (m, 2H, ArH), 7.26 (d, 1H, ArH).

Part 2: Preparation of N-(2-chloro-5-methoxyphenyl)-N'-(3-methylthiophenyl)N'-methylguanidine hydrocloride A mixture of N-methyl-N-cyano-3-methylthioaniline, prepared in Part 1 of this Example above, (1.0 g, 5.61 mmol) and 2-chloro-5-methoxyaniline hydrochloride (1 g, 5.15 mmol) in xylenes (5 ml) was heated to reflux for 3 hours. The cooled reaction mixture was concentrated and the residue was treated with dichloromethane (5 ml) followed by ether (20 ml). The solid separated was filtered, dried. Yield 542 mg (26%); mp: 194–196° C.; HPLC 98.7% @ 18.7 minutes; TLC (CHCl$_3$:MeOH; 4:1) Rf=0.61; $^1$H-NMR (CD$_3$OD) δ 2.52 (s, 3H, SMe), 3.48 (s, 3H, NMe), 3.8 (s, 3H, OMe), 6.98 (m, 2H, ArH), 7.21 (d, 1H, ArH), 7.33 (m, 2H, ArH), 7.43 (m, 2H, ArH).

Part 3: Preparation of N-(3-chloro-5-methoxyphenyl)-N'-(3-methylsulfinylphenyl)-N'-methylguanidine hydrochloride To a solution of N-(2-chloro-5-methoxyphenyl)-N'-(3-methylthiophenyl)-N'-methylguanidine hydrochloride, prepared in Part 2 of this Example above, (0.4 g, 1.07 mmol) in methanol (5 ml) and water (3 ml) was added sodium periodate (275 mg, 1.29 mmol) and the reaction mixture was stirred at room temperature overnight. Upon filtering the solid separated, the residue washed with dichloromethane (10 ml) and the filtrate concentrated. The solution was made alkaline with sodium hydroxide (10 ml, 1N) and repeatedly extracted with dichloromethane (3×10 ml), washed with organic layer with water (2×5 ml), dried and concentrated. The crude product was purified by column using chloroform initially and gradually to chloroform containing 12% methanol to isolate the title compound. Yield 300 mg (72%); mp: 72–74°; HPLC 99.3% @13.3 minutes; TLC (CHCl$_{13}$: MeOH; 4:1) Rf-0.38; $^1$H-NMR (CD$_3$OD) δ 2.83 (s, 3H, SOMe), 3.48 (s, 3H, NMe), 3.8 (s, 3H, OMe), 6.76 (m, 2H, ArH), 7.33 (m, 1H, ArH), 7.61 (m, 3H, ArH), 7.78 (s, 1H, ArH).

EXAMPLE 5

Preparation of (R)-N-(2-chloro-3-methylthiophenyl)-N'-(3-methylsulfinylphenyl)-N'-methylguanidine acetate To a solution of (R)-N-(2-chloro-3-methylthiophenyl)-N'-(3-methylsulfinylphenyl)-N'-methylguanidine (123 mg, 0.34 mmol) in chloroform (5 ml) in ice bath (5–10° C.) was added acetic acid in chlorofom (1M, 0.45 ml) was added slowly and stirred for 15 mins, concentrated under reduced pressure followed by coevaporation with dichloromethane (3×5 ml) to obtain a white low melting solid of acetate salt (140 mg); 1H-NMR(CD$_3$OD) δ 1.92 (s, 3H, MeCO), 2.47 (s, 3H, SMe), 2.82 (s, 3H, S(O)Me), 3.50 (s, 3H, NMe), 7.11 (m, 2H, Ar), 7.37 (dd, 1H, Ar), 7.62–7.66 (m, 3H, Ar), 7.78 (m, 1H, Ar); Anal. Calcd. For C$_{18}$H$_{22}$ClN$_3$O$_3$S$_2$ 0.5H2O; C: 49.43, H: 5.26, N: 9.61; Found: C: 49.63, H: 5.33, N: 9.49.

EXAMPLE 6

Preparation of (S)-N-(2-chloro-3-methylthiophenyl)-W-(3-methylsulfinylphenyl)-N'-methylguanidine acetate Following a similar procedure as disclosed in Example 5 above, (S)-N-(2-chloro-3-methylthiophenyl)-N'-(3-methylsulfinylphenyl)-N'-methylguanidine (125 mg, 0.34 mmol) was converted to the acetate salt (146 mg); 1H-NMR (CD$_3$OD) δ 1.94 (s, 3H, MeCO), 2.49 (s, 3H, SMe), 2.84 (s, 3H, S(O)Me), 3.52 (s, 3H, NMe), 7.13 (m, 2H, Ar), 7.4 (dd, 1H, Ar), 7.64–7.68 (m, 3H, Ar), 7.80 (m, 1H, Ar); Anal. Calcd. For C$_{18}$H$_{22}$ClN$_3$O$_3$S$_2$ 0.5H$_2$O; C: 49.43, H: 5.26, N: 9.61; Found: C: 49.15, H: 5.25, N: 9.41.

EXAMPLE 7

Chiral Synthesis of (R)-N-(2-chloro-3-methylthiophenyl)-N'-(3-methylsulfinylphenyl)-N'-methylguanidine A. Preparation of (R)-3-methylsulfinyl-N-methylaniline hydrochloride 1. Oxidation Step: (R)-3-Methylsulfinyl-N-methylaniline To a solution of (R)-(−)-(8,8-dichloro-10-camphorsulfonyl)oxaziridine (1.65 g, 5.53 mmol) in carbon tetrachloride (50 ml) under stirring was added N-methyl-3-methylthioaniline (1.0 g, 7.17 mmol) in 5 ml of carbon tetrachloride at room temperature. The reaction mixture was stirred for overnight (~18 hours) and the reaction mixture was filtered to remove the solid separated, washed with carbon tetrachloride (10 ml) and the combined filtrate was concentrated. The residue was chromatographed on silica gel using gradually a mixtures of hexanes:ethyl acetate initially 4:1, to remove the unreacted starting material. Finally elution with chloroform and later chloroform containing 2% methanol eluted the sulfoxide and the fractions were combined, concentrated under reduced pressure to yield (R)-3-Methylsulfinyl-N-methylaniline as an oil in quantitative yield. 0.97 gm; TLC CHCl$_3$:MeOH 19:1; Rf=0.48; Purity 92% ee by $^1$H-NMR; $^1$H-NMR (CDCl$_3$) δ 2.71 (s, 3H, SOMe, 2.87 (s, 3H, NMe), 6.66 (dd, 1H), 6.81 (dd, 1H), 6.92 (s, 1H), 7.28 (m, 1H).

2. Conversion to hydrochloride

The free amine of (R)-3-Methylsulfinyl-N-methylaniline (0.97g, 5.73 mmol), obtained as above, was dissolved in dichloromethane (15 ml), cooled in an ice water bath and to this solution anhydrous hydrogen chloride in methanol (1M, 6ml) was added slowly with vigorous stirring to enable thorough mixing. Stirred for 30 mins as such, concentrated under reduced pressure and dried under high vacuum to afford (R)-3-methylsulfinyl-N-methylaniline hydrochloride as hygroscopic colorless fluffy solid (1.12 g) in almost quantitative yield. $^1$H-NMR (CD$_3$OD) δ 2.87 (s, 3H, S(O)Me), 3.15 (s, 3H, NMe) 7.65 (m, 1H,), 7.77 (m, 1H), 7.83 (m, 1H).

B. Condensation Step: (R)-N-(2-chloro-3-methylthiophenyl)-N'-(3-methylsulfinylphenyl)-N'-methylguanidine hydrochloride In a single necked round bottomed flask was placed a solution of (R)-3-methylsulfinyl-N-methylaniline hydrochloride (1.12 g, 5.64 mmol) in dichloromethane (20 ml). With stirring 2-chloro-5-methylthiophenylcyanamide (1.12 g, 5.44 mmol) and toluene (20 ml) were added. The flask was fitted with a Vigreaux column attached to a short distillation setup for collecting the solvent distilled during the reaction. This mixture was slowly heated in an oil bath to 115–120° C. and the dichloromethane distilled was collected. After the complete distillation of dichloromethane, the reaction mixture was maintained at 115–120° C. for 1 hour, cooled to room temperature and the solvent was removed under reduced pressure. The residue was purified by silica gel column chromatography (charged with some charcoal for decolorization at the top of the column) using initially chloroform and gradually changed to chloroform containing 5% methanol as eluents. The almost colorless product, (R)-N-(2-chloro-3-methylthiophenyl)-N'-(3-methylsulfinylphenyl)-N'-methylguanidine hydrochloride, obtained upon concentration of fractions was dried under high vacuum. 1.1 g (51%); TLC CHCl$_3$:MeOH 4:1; Rf=0.33; $^1$H-NMR (CDCl$_3$) δ 2.40 (s. 3H, SMe), 2.72 (s, 3H, S(O)Me), 3.55 (s, 3H, NMe), 6.84 (2s,2H), (7.11 (d, 1H), 7.35 (m, 3H), 7.52 (s, 1H); Purity 72.7% ee by $^1$H-NMR; Chiral HPLC 75.8% ee @ 32.6.

C. Conversion of the Hydrochloride Salt to the Free Base (R)-N-(2-chloro-3-methylthiophenyl)-N'-(3-methylsulfinylphenyl)-N'-methylguanidine hydrochloride (0.56 g) was dissolved in chloroform (25 ml) and methanol (3 ml) added to get a clear solution and this was treated with sodium hydroxide (1N, 2×25 ml) in a separating funnel. The organic layer was separated and the aqueous layer was extracted with chloroform (20 ml). Combined organic layer was washed with water (25 ml) and passed through a bed of sodium chloride to remove any solid suspensions and the filtrate was concentrated to yield the free base of (R)-N-(2-chloro-3-methylthiophenyl)-N'-(3-methylsulfinylphenyl)-N'-methylguanidine (0.37 g., 73%); Chiral HPLC 76.5% ee @ 16.45; HPLC 97.7% @ 14.5 mins; $^1$H-NMR (CD$_3$OD) δ 2.46 (s, 3H, SMe), 2.77 (s, 3H, S(O)Me), 3.47 (s, 3H, NMe), 6.81 (dd, 1H), 6.87 (dd, 1H), 7.28 (d, 1H), 7.50 (m, 3H), 7.68 (s, 1H).

The free base obtained was crystallized from a mixture of hexanes and dichloromethane to give white crystalline solid of (R)-N-(2-chloro-3-methylthiophenyl)-N'-(3-methylsulfinylphenyl)-N'-methylguanidine (0.15 g) with increased enantiomeric purity; m. p. 118–120° C.; Chiral HPLC 94.5% ee @ 16.9 mins.

EXAMPLE 8

Rat Rotarod Motor Coordination Test

A. Hydrochloride salt of (±)-N-(2-chloro-5-methylthiophenyl)-N'-(3-methylsulfinylphenyl)-N'-methylguanidine.

The effects of the hydrochloride salt of (t)-N-(2-chloro-5-methylthiophenyl)-N'-(3-methylsulfinylphenyl)-N'-methylguanidine (compound (I)) on motor coordination were assessed using the rotarod test. Drug solutions were administered i.v. through the tail vein of test rats in a volume of 5.0 ml/kg at a rate of 1 ml/min. The percentage of animals in each treatment group that fell from the rotarod at each of the four time points tested is summarized in the following Table I. Control was 20% C.D. N in each of the Tables below specifies the number of animals in each test group.

TABLE I

| Time Dose | 15 min. | 60 min. | 120 min. | 180 min. | N |
| --- | --- | --- | --- | --- | --- |
| Control | 29 | 14 | 0 | 14 | 7 |
| 8.0 mg/kg | 38 | 50 | 25 | 25 | 8 |
| 12.0 mg/kg | 100 | 100 | 75 | 50 | 4 |

Figure 1:
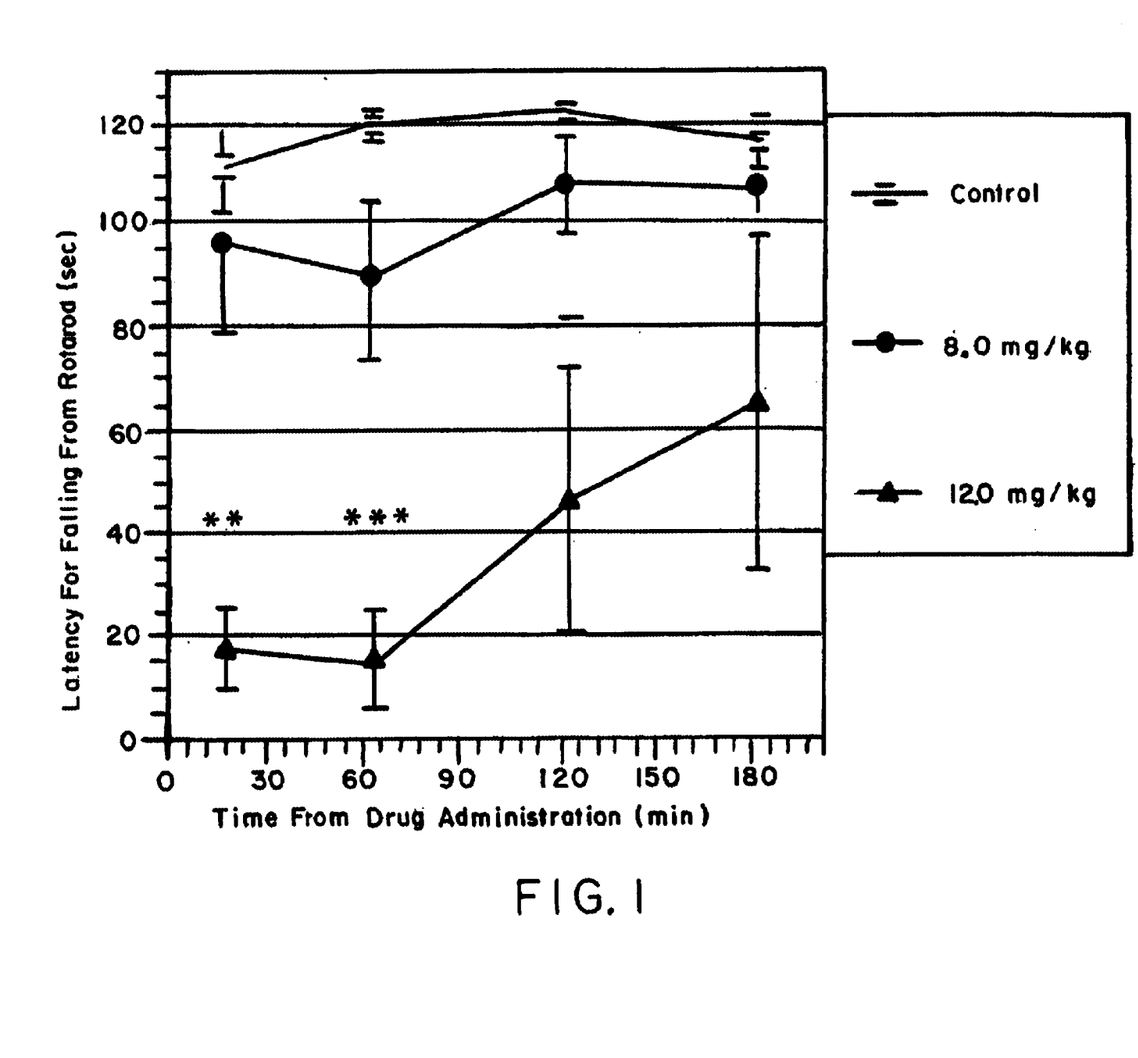
FIG. 1 shows the time course effects of the hydrochloride salt of (±)-N-(2-chloro-5-methylthiophenyl)-N'-(3-methylsulfinylphenyl)-N'-methylguanidine in the rotarod test of Example 8 which follows.

The latency for falling from the rotarod was statistically analyzed using analysis of variance (ANOVA), and a Neumann Keuls post-hoc was applied when appropriate. Rats in the 12.0 mg/kg drug group had significantly shorter latency for falling from the rotarod than the rats in the control group at the 15 minute, 60 minute and 120 minute time points. By 180 minutes, no statistically significant differences in falling times were observed. The results (expressed as mean ±s.e.m.) are shown in FIG. 1 of the drawings. In FIG. 1, "" designates P<0.01 and "*" designates P<0.001.

The following behavioral effects also were observed with administration of the hydrochloride salt of (±)-N-(2-chloro- 5-methylthiophenyl)-N'-(3-methylsulfinylphenyl)-N'-methylguanidine: animals in both drug groups (i.e. 8.0 mg/kg and 12.0 kg/mg dosages) showed increased locomotion at 120 minutes. Some animals displayed mild head weaving. Two animals in the 12.0 mg/kg group died within 15 minutes after injection, a third animal died 60 minutes after injection. Pre-testing doses of 20.0 and 16.0 mg/kg were lethal.

B. Acetate salt of (−)-N-(2-chloro-5-methylthiophenyl)-N'-(3-methylsulfinylphenyl)-N'-methylguanidine (compound (IA)).

The acetate salt of (−)-N-(2-chloro-5-methylthiophenyl)-N'-(3-methylsulfinylphenyl)-N'-methylguanidine was also tested in the same rotarod assay protocol as described in Part A above. Drug solutions were administered i.v. through the tail vein in a volume of 5 ml/kg at a rate of 1 ml/min. The percentage of animals in each treatment group that fell from the rotarod at each time point is summarized in the following Table II. In Table II, Control (1) is 60 mM Acetate Buffer in 0.3M mannitol at 0.06 and 0.125 mg/kg doses and Control (2) is 60 mM Acetate Buffer in 0.3M mannitol at 0.25 and 0.5 mg/kg doses.

TABLE II

| Time Dose | 15 min. | 60 min. | 120 min. | 180 min. | N |
|---|---|---|---|---|---|
| Control (1) | 0 | 13 | 13 | 0 | 8 |
| Control (2) | 0 | 13 | 13 | 0 | 8 |
| 2.0 mg/kg | 0 | 0 | 14 | 0 | 7 |
| 4.0 mg/kg | 14 | 0 | 14 | 14 | 7 |
| 8.0 mg/kg | 78 | 33 | 22 | 22 | 9 |
| 12.0 mg/kg | 78 | 11 | 11 | 11 | 9 |

Figure 2:
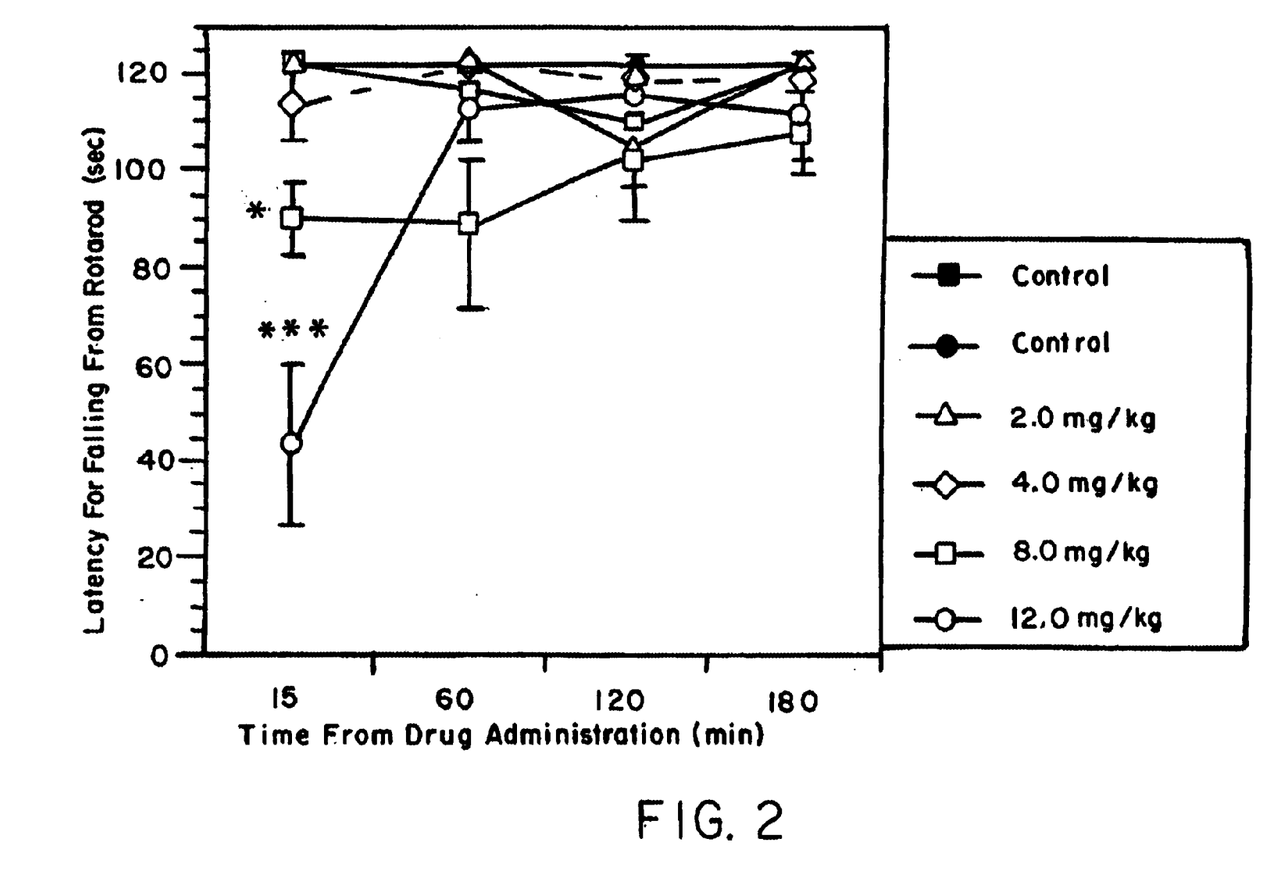
FIG. 2 shows the time course effects of the acetate salt of (−)-N-(2-chloro-5-methylthiophenyl)-N'-(3-methylsulfinylphenyl)-N'-methylguanidine in the rotarod test of Example 8 which follows.

The latency for falling from the rotarod was statistically analyzed using analysis of variance (ANOVA), and a Neuman Keuls post-hoc was applied when appropriate. No statistical significance was found between control animals and the animals in the 0.06 and 0.125 mg/kg groups at any time point. Rats in the remaining groups at the 15 and 60 minute time points had significantly shorter latencies for falling from the rotarod than rats in the control groups. At 120 minutes, no statistically significant differences in falling times were observed in the two low dose groups. Full recovery was not achieved by the animals in the high dose groups even at 180 minutes. These results are summarized in FIG. 2 of the drawings. In FIG. 2, Controls (1) and (2) are the same as specified above. The results (expressed as mean +s.e.m.) are shown in FIG. 2 of the drawings, where "*"designates $P<0.05$ and "***" designates $P<0.001$ compared to group controls.

C. Acetate salt of (+)-N-(2-chloro-5-methylthiophenyl)-N'-(3-methylsulfinylphenyl)-N'-methylguanidine (compound (IB)).

The acetate salt of (+)-N-(2-chloro-5-methylthiophenyl)-N'-(3-methylsulfinylphenyl)-N'-methylguanidine was also tested in the same rotarod assay protocol as described in Part A above. Drug solutions were administered i.v. through the tail vein in a volume of 5 ml/kg at a rate of 1 ml/min. The percentage of animals in each treatment group that fell from the rotarod at each time point is summarized in the following Table III. In Table III, Control (1) is 60 mM Acetate Buffer in 0.3M mannitol at 0.06 and 0.125 mg/kg doses and Control (2) is 60 mM Acetate Buffer in 0.3M mannitol at 0.25 and 0.5 mg/kg doses.

TABLE III

| Time Dose | 15 min. | 60 min. | 120 min. | 180 min. | N |
|---|---|---|---|---|---|
| Control (1) | 0 | 13 | 13 | 0 | 8 |
| Control (2) | 0 | 13 | 13 | 0 | 8 |
| 2.0 mg/kg | 0 | 0 | 0 | 0 | 7 |
| 4.0 mg/kg | 29 | 29 | 57 | 57 | 7 |
| 8.0 mg/kg | 100 | 100 | 100 | 67 | 8 |
| 12.0 mg/kg | 100 | 100 | 100 | 100 | 6 |

Figure 3:
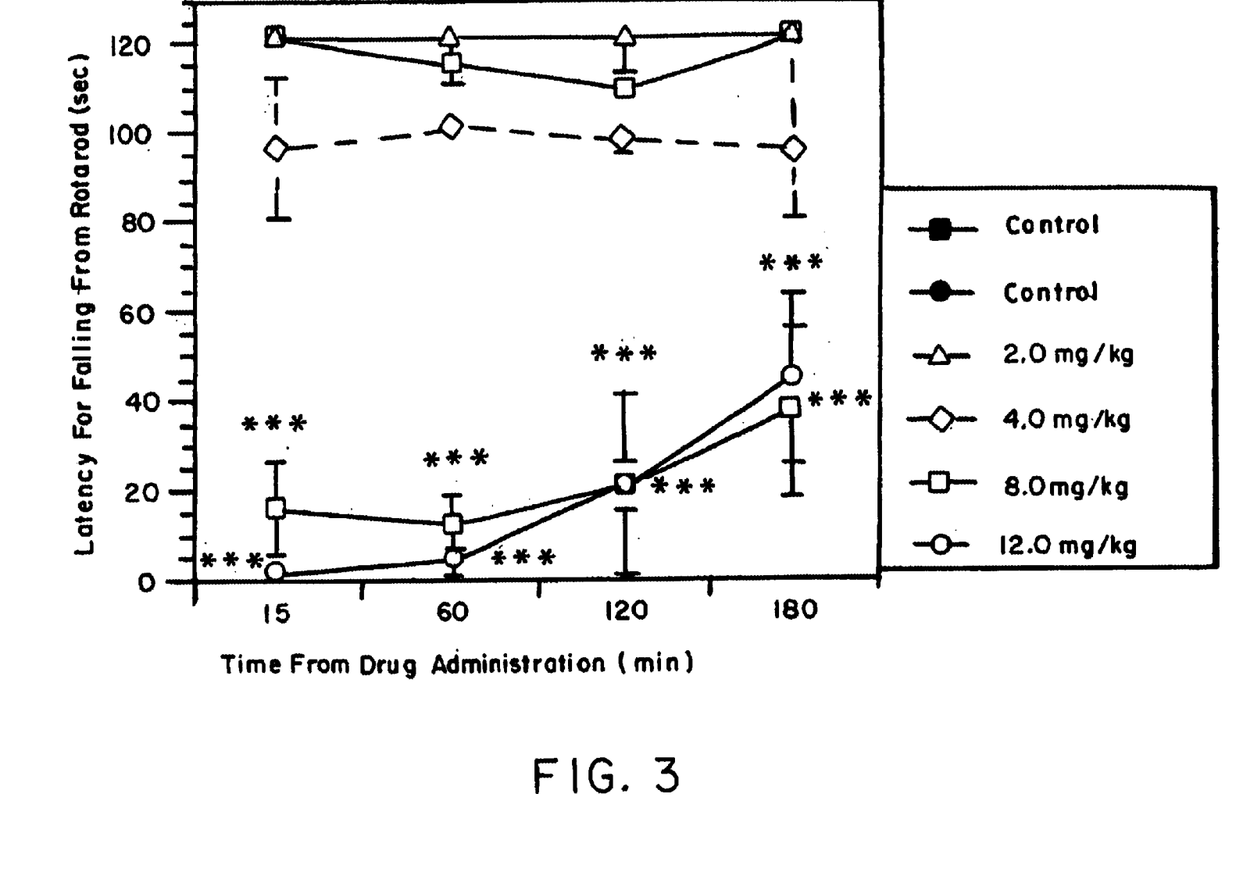
FIG. 3 shows the time course effects of the acetate salt of (+)-N-(2-chloro-5-methylthiophenyl)-N'-(3-methylsulfinylphenyl)-N'-methylguanidine in the rotarod test of Example 8 which follows.

The latency for falling from the rotarod was statistically analyzed using analysis of variance (ANOVA), and a Neuman Keuls post-hoc was applied when appropriate. No statistical significance was found between control animals and the animals in the 0.06 and 0.125 mg/kg groups at any time point. Rats in the remaining groups at the 15 and 60 minute time points had significantly shorter latencies for falling from the rotarod than rats in the control groups. At 120 minutes, no statistically significant differences in falling times were observed in the two low dose groups. Full recovery was not achieved by the animals in the high dose groups even at 180 minutes. The results (expressed as mean ±s.e.m.) are shown in FIG. 3 of the drawings, where "***" designates $P<0.001$ compared to group controls. Controls (1) and (2) are the same as specified above for Table 3.

The results for compounds of the invention can be compared to those obtained for MK-801, i.e. (+)-5-methyl-10,11-dihydro-5H-dibenzo[a,d]cyclohepten-5,10-imine maleate. In the rotarod test for MK-801, drug solutions were administered i.v. through the tail vein of each test rat in a volume of 5 ml/kg at a rate of 1 ml/min. The control was 0.9% saline solution. The percentage of animals in each treatment that fell from the rotarod at each test point is summarized in the following Table IV:

TABLE IV

| Time Dose | 15 min. | 60 min. | 120 min. | N |
|---|---|---|---|---|
| Control | 13 | 13 | 13 | 8 |
| 0.01 mg/kg | 38 | 13 | 25 | 8 |
| 0.05 mg/kg | 86 | 57 | 29 | 7 |

EXAMPLE 9

Irwin General Behavior Screen

The hydrochloride salt of (±)-N-(2-chloro-5-methylthiophenyl)-N'-(3-methylsulfinylphenyl)-N'-methylguanidine (compound (I)) was tested in the Irwin general behavior screen with the lowest dose determined at which definite behavioral effects were observed in the test rats, especially excitation effects. See S. Irwin, Animal and Clinical Pharmacologic Techniques in Drug Evaluation, pages 36–54 (Year Book Medical Publishers, Chicago), which details the protocol of the Irwin behavior screen. The following results were obtained: at dose of 4 mg/kg i.v. administration, excitation (120–180') sterotypies (sniffing 60–180') fore-paw treading (120') loss of traction (2 of 3, 120'); at dose of 16 mg/kg i.v. administration excitation (30–180') sterotypies (head-weaving to 180') fore-paw treading (to 180') loss of traction (to 180') hypothermia.

EXAMPLE 10

Rat MCAO Ischemia Model

A. The hydrochloride salt of (±)-N-(2-chloro-5-methylthiophenyl)-N'-(3-methylsulfinylphenyl)-N'- methylguanidine (compound (I)) was tested in the rat MCAO ischemia model with % reduction in total lesion volume (mm³) determined by the following protocol.

Rats were anaesthetized with isoflurane and focal ischemia was induced by directly ligating the main trunk of MCA using a bipolar electrocoagulor. Coronal sections (seven sections, 2.0 mm intervals) were collected and incubated in 2,3,5-triphenyltetrazolium chloride (TTC) solution for 15 minutes at 37° C., then fixed in 4% paraformaldehyde solution in the dark at 4° C. for at least 48 hours. Seven sections of each brain were photographed and analyzed. The areas that were not stained red with TTC were measured as infarction.

The test animals were treated with the test compound and control (mannitol) as follows. Ten minutes after the MCAO incident the test animals were administered (i.v. infusion/10 minutes) with one third of the total dose of the test compound (total doses specified below); 1 hour after that first dosing the test animals were given another one third of the total dose of the test compound; and then 2 hours after that first dosing the test animals were given another one third of the total dose of the test compound. Mannitol was administered to the control group at the first dosing only.

The following results were obtained:

46% at dose of 9 mg/kg

32% at dose of 4.5 mg/kg

24% at dose of 2.25 mg/kg

B. The acetate salt of (−)-N-(2-chloro-5-methylthiophenyl)-N'-(3-methylsulfinylphenyl)-N'-methylguanidine (compound (IA)) was tested in the rat MCAO ischemia model with % reduction in total lesion volume determined by the same MCAO assay protocol specified in Part A above.

Sprague-Dawley rats with body weights of 270–320 grams were used in the study.

The following results were obtained expressed as % reduction in total average lesion volume (mm³) by the specified dosage (values below refer to total dose administered; n designates number of test rats):

1% at 4.5 mg/kg (n=8)

22% at 9 mg/kg (n=8)

C. The acetate salt of (+)-N-(2-chloro-5-methylthiophenyl)-N'-(3-methylsulfinylphenyl)-N'-methylguanidine (compound (IB)) was also tested in the rat MCAO ischemia model with % reduction in total lesion volume determined by the same protocol as specified in Part A above. Sprague-Dawley rats with body weights of 270–320 grams were used in the study. The following results were obtained expressed as % reduction in total average lesion volume (mm³) by the specified dosage (values below refer to total dose administered; n designates number of test rats):

23% at 2.25(mg/kg) (n=12)

32% at 4.5 mg/kg (n=8)

34% at 9.0 mg/kg (n=8)

EXAMPLE 11

Rat Pup Hypoxia-ischemia Model

A. The hydrochloride salt of (±)-N-(2-chloro-5-methylthiophenyl)-N'-(3-methylsulfinylphenyl)-N'-methylguanidine was tested in the rat pup hypoxia-ischemia model with % reduction in total lesion volume determined at the specified test dose. A rat pup hypoxia-ischemia assay protocol of the following protocol was employed.

8 day-old rat pups weighing 17–23 grams were anaesthetized with isoflurane and the left common carotid artery ligated. Immediately prior to the hypoxia-ischemia (H-I) insult a test group of animals was injected intraperitoneally with 2 mg/kg, 5 mg/kg or 10 mg/kg of the test compound and a control group was treated with a corresponding dose of mannitol. Then, immediately after the H-I insult, the animals received a second equivalent dose, i.e. the test group of animals was injected intraperitoneally with 2 mg/kg (total 4 mg/kg administered in the two doses), 5 mg/kg (total 10 mg/kg administered in the two doses) or 10 mg/kg (total 20 mg/kg administered in the two doses) of the test compound and a control group was treated with a corresponding dose of mannitol. The animals were then allowed to recover for 1–2 hours and then exposed to 7.8% $O_2$ in nitrogen for 78 minutes in an incubator at 36.5° C. The rat pups were returned to mothers immediately after the H-I insult. The animals were sacrificed two days after H-I insult, their brain was removed and cut into four 2 mm thick slices prior to staining with 2% 2,3,5-triphenyltetrazolium chloride (TTC) solution. The sections were then fixed with 4% paraformaldehyde solution in the dark at 4° C. for at least 48 hours. Four sections from each brain were imaged and analyzed using the IPLab system. The lesion area which was not stained red with TTC was measured as infarction.

The following results were obtained:

100% at i.p. total dose of 20 mg/kg

60% at i.p. total dose of 10 mg/kg

B. The acetate salt of (+)-N-(2-chloro-5-methylthiophenyl)-N'-(3-methylsulfinylphenyl)-N'-methylguanidine was also tested in the rat pup hypoxia-ischemia model with % reduction in total lesion volume determined by the same protocol as specified in Part A above, except the rat pups were exposed to 7.8% $O_2$ in nitrogen for 85 minutes. The following results were obtained:

93% at i.p. total dose of 20 mg/kg

78% at i.p. total dose of 10 mg/kg

The foregoing description of the invention is merely illustrative thereof, and it is understood that variations and modifications can be made without departing from the spirit or scope of the invention as set forth in the following claims.

What is claimed is:

1. N-(2-chloro-5-methylthiophenyl)-N-(3-methylsulfinyl phenyl)-N'-methylguanidine, or a pharmaceutically acceptable salt thereof.

2. An optically active stereoisomer of a compound of claim 1.

3. The compound or a pharmaceutically acceptable salt thereof.

4. The compound or a pharmaceutically acceptable salt thereof.

5. A pharmaceutical composition comprising a therapeutically effective amount of a compound of any one of claims 1 through 4 and a pharmaceutically acceptable carrier.

6. A compound of any one of claims of claims 1 through 4 that is radiolabelled.

7. A pharmaceutical composition that comprises an enantiomer of claim 2 that is present in at least about 90 percent enantiomeric purity.

8. A pharmaceutical composition of claim 2 wherein the enantiomer is present in at least about 95 percent enantiomeric purity.

* * * * *